United States Patent
Willemse et al.

(12)

(10) Patent No.: US 7,853,355 B1
(45) Date of Patent: Dec. 14, 2010

(54) PHARMACEUTICAL DISPENSING SYSTEM FOR MEDICAMENT AND PRE-PACKAGED MEDICATION

(76) Inventors: Waldemar Willemse, 12815 Stone Canyon Rd., Poway, CA (US) 92064; Clasina Aletta Willemse, 12815 Stone Canyon Rd., Poway, CA (US) 92064; Werner Waldemar Willemse, 15619 Alcachofa Ave. #D, San Diego, CA (US) 92128

( * ) Notice: Subject to any disclaimer, the term of this patent is extended or adjusted under 35 U.S.C. 154(b) by 0 days.

(21) Appl. No.: 11/482,889

(22) Filed: Jul. 7, 2006

(51) Int. Cl.
*G06F 17/00* (2006.01)

(52) U.S. Cl. ............... 700/243; 700/242; 700/241; 700/236; 700/232

(58) Field of Classification Search .......... 700/231–244
See application file for complete search history.

(56) References Cited

U.S. PATENT DOCUMENTS

| | | | |
|---|---|---|---|
| 3,917,045 A | 11/1975 | Williams | |
| 4,901,841 A | 2/1990 | Haggerty | |
| 5,027,938 A | 7/1991 | Haggarty et al. | |
| 5,213,232 A * | 5/1993 | Kraft et al. | 221/277 |
| 5,317,645 A | 5/1994 | Perozek | |
| 5,337,919 A | 8/1994 | Spaulding | |
| 5,768,327 A | 6/1998 | Pinto | |
| 5,798,020 A | 8/1998 | Coughlin | |
| 5,860,563 A | 1/1999 | Guerra | |
| 5,884,806 A * | 3/1999 | Boyer et al. | 221/75 |
| 5,907,493 A | 5/1999 | Boyer | |
| 6,578,734 B1 | 6/2003 | Coughlin | |
| 6,592,005 B1 * | 7/2003 | Coughlin et al. | 221/129 |
| 6,631,826 B2 | 10/2003 | Pollard | |
| 6,681,149 B2 | 1/2004 | William | |
| 6,735,497 B2 * | 5/2004 | Wallace et al. | 700/231 |
| 6,892,941 B2 * | 5/2005 | Rosenblum | 235/383 |
| 6,899,144 B1 | 5/2005 | Geltser | |
| 6,905,046 B2 | 6/2005 | Coughlin | |
| 6,910,601 B2 | 6/2005 | Thomas | |
| 6,974,049 B2 | 12/2005 | Williams et al. | |
| 6,974,050 B2 | 12/2005 | Williams | |
| 7,228,198 B2 * | 6/2007 | Vollm et al. | 700/235 |
| 7,289,879 B2 * | 10/2007 | William et al. | 700/235 |
| 2006/0088196 A1 * | 4/2006 | Popovich et al. | 382/128 |
| 2006/0124656 A1 * | 6/2006 | Popovich, Jr. | 221/9 |
| 2006/0161296 A1 * | 7/2006 | Shoenfeld | 700/242 |

* cited by examiner

*Primary Examiner*—Gene Crawford
*Assistant Examiner*—Michael K Collins
(74) *Attorney, Agent, or Firm*—John R. Ross, III; John R. Ross (57) ABSTRACT

This invention focuses on resolving outstanding problems of pharmaceutical dispensing systems. A need for dispensing of both medicaments and pre-packed medications has been addressed. This invention comprises an accurate counting system for multiple concurrently dispensed medicaments. Accurate, high speed medicament dispensing with little or no jam ups is achieved. Self recovery is provided to prevent medicament over counts. Machine self learn modes replace manual intervention by pharmacy personnel. Concurrent multi-tasking is provided and a quick action robotic arm further expedites the dispensing process. A touch screen computer is provided for coordinating the individual modules and overall control. The apparatus covers internal security and restricts access to unauthorized persons.

14 Claims, 8 Drawing Sheets

PHARMACEUTICAL DISPENSING SYSTEM FOR MEDICAMENT AND PRE-PACKAGED MEDICATION

CROSS REFERENCE TO RELATED APPLICATIONS

| | | |
|---|---|---|
| 7,014,063 B2 | March 2006 | Shows |
| 6,974,050 B2 | December 2005 | Williams |
| 6,974,049 B2 | December 2005 | Williams |
| 6,971,544 B2 | December 2005 | Williams |
| 6,971,541 B2 | December 2005 | Williams |
| 6,910,601 B2 | June 2005 | Thomas |
| 6,905,046 B2 | June 2005 | Coughlin |
| 6,899,148 B1 | May 2005 | Geltser |
| 6,899,144 B1 | May 2005 | Geltser |
| 6,883,681 B1 | April 2005 | Coughlin |
| 6,742,671 B2 | June 2004 | Hebron |
| 6,722,525 B1 | April 2004 | Boyer |
| 6,667,473 B1 | December 2003 | Worthington |
| 6,659,304 B1 | December 2003 | Geltser |
| 6,631,826 B2 | October 2003 | Pollard |
| 6,625,967 B1 | July 2004 | Hebron |
| 6,625,952 B1 | September 2004 | Chudney |
| 6,578,734 B1 | June 2003 | Coughlin |
| 6,578,733 B2 | June 2003 | Geltser |
| 6,592,005 B1 | July 2003 | Coughlin |
| 6,497,339 B1 | December 2002 | Geltser |
| 6,421,584 B1 | July 2002 | Norberg |
| 6,370,215 B1 | April 2002 | Pinto |
| 6,161,721 | December 2000 | Kudera et al. |
| 6,116,461 | September 2000 | Broadfield |
| 6,085,938 | July 2000 | Coughlin |
| 5,907,493 | May 1999 | Boyer |
| 5,897,024 | April 1999 | Coughlin |
| 5,884,806 | March 1999 | Boyer |
| 5,873,488 | February 1999 | Guerra |
| 5,860,563 | January 1999 | Guerra |
| 5,798,020 | August 1998 | Coughlin |
| 5,768,327 | June 1998 | Pinto |
| 5,762,235 | June 1998 | Coughlin |
| 5,671,262 | September 1997 | Boyer |
| 5,638,417 | June 1997 | Boyer |
| 5,520,450 | May 1996 | Colson |
| 5,473,703 | December 1995 | Smith |
| 5,463,839 | November 1995 | Strange |
| 5,337,919 | August 1994 | Spaulding |
| 5,317,645 | May 1994 | Perozek |
| 5,213,232 | May 1993 | Kraft |
| 5,027,938 | June 1991 | Haggarty |
| 4,901,841 | February 1990 | Haggarty |
| 3,985,264 | October 1976 | Shaw |
| 3,917,045 | November 1975 | Williams |

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION (1) Field of Invention

Pharmacies normally dispense medication based on patient's prescriptions as either pre-packaged where the correct number of doses are pre packed in a container, or as medicament where a prescribed number of pills are counted into a vial from a supply container. Several inventions have been made over the last 30 years to automate segments of the counting and dispensing process.

(2) Description of the Related Prior Art Including Information Disclosure

Automatic pharmacy dispensing systems have improved over the last three decades. Prior art has, however, not resolved the problems as listed below.

Prior art medicament counting problems:

Prior art using basic one emitter and one receiver sensors:

These basic light beam medicament counters have two main drawbacks. The first drawback is that a restrictive channel must be used to force each and every medicament through the light beam. Those skilled in the art would agree this leads to jam ups. Further, these restrictive channels are usually difficult to get to inside the dispenser mechanism, requiring emptying of the medicament supply bin. Additionally, pharmacy personnel have to set up these restrictive channels for different medicament sizes. The second drawback is that if the restrictive channel is not narrow enough at the counting point, two or more medicaments, one in the other's shadow, can be counted as one.

Those skilled in the art would agree that the counting process is eased with greater separation gaps between medicaments. This is readily achievable through free fall. Free fall, by definition, is not possible through a restrictive channel.

Prior art, (U.S. Pat. No. 6,592,005 B1, Jul. 7, 2003, Couglin et al) relies on widening of a single light source and finally concentrating the single light source after sensing into a single receiver. The aforementioned does not provide the ability to discern what specific areas, or beams within the sensing plane was affected by medicaments passing through. The above patent claims the emitter and detector on opposite sides of the detection plane. It should be noted that all claims are to a single medicament being sensed a time since medicaments could be erroneously counted when moving adjacent one another through the sensing plane. Also the physically bulky nature of opposed through-beam sensor configurations imposes limitations on the layout and technology used in a very critical area.

Prior art using wide beams with array receiver sensors, where individual elements of the array, or pixels, can be individually accessed:

Prior art U.S. Pat. No. 5,768,327, July 1998, Itzhak Pinto et al. shows two charge coupled array sensors, spaced relative to each other at 90 degrees, used for a free fall bulk, very large volume, medicament counter. The physical layout of two sets of sensor arrays is cumbersome and costly. In the disclosure it becomes apparent that the device was not intended to be a unit accurate counter. Note in this patent's disclosure, the adjustable fall distance pipe to reduce the chances of miscounting medicaments during tumbling. It should be noted that more recent patents to the same assignee have moved the emphasis from relying only on two axis array detection systems to improving singulation.

Prior art and medicament dispensing problems:

Those skilled in the art would agree that prior art has a direct relationship between singulation and jam ups. The narrower the passageway, the better the singulation, however also the greater the probability of a jam occurring. Prior art U.S. Pat. No. 5,213,232, May 1993, Kraft et al. and U.S. Pat. No. 5,884,806 Mar. 1999, Boyer et al. show the advantages of Archimedes screw dispensers but, as disclosed, jam problems exist. There is thus a need over prior art for a medicament dispenser with speed, good singulation and that does not jam. Preferably it should do it's own set up in a learn mode.

Prior art lacks dispensing error recovery systems.

Even with good singulation, accurate counting and good control algorithms, the possibility always exists that few medicaments may be teetering on the edge and instead of dispensing one last medicament to complete the needed count, a few more will fall into the vial. Some prior art systems slow down to a snail's pace when nearing the full count. While this improves the problem it does so at a dispensing time cost and the over count problem is still not eliminated.

Prior art lacks dispensing of medicament dispensing and prepackaged medication in one system:

Prior art lacks adequate collation area suitable for medicament vials and pre-packed medication.

Prior art does not provide both medicament and pre-packaged dispensing from one system. The existing pharmacy dispensing automats are thus only half automats, leaving mostly the pre-packaged dispensing to be done manually. Pre-packaged dispensing capability is critical for the export market.

Efficient use of pharmacy floor space and running costs:

Prior art is not modular and thus can not be customized to pharmacy floor layouts. Without modularization automation can not grow as customers requirements and their budgets grow. Prior art systems are complicated and thus costly to purchase and run. This makes return of investment more difficult to achieve.

Although, over the last three decades, the automatic pharmacy dispensing automats' have made great strides forward, the problems highlighted above have not been solved in prior art.

BRIEF SUMMARY OF THE INVENTION

The system comprises, empty vial holding bins with vial retrieval, labeling, robotic arms for moving empty vials to a plurality of medicament supply bins with dispensers, medicament counter, capping station and an a plurality of output holding stations. Pre-packaged medication is retrieved from holding conveyors.

Of special significance are resolved problems:

Resolving medicament counting problems:

By orienting the medicaments falling through a counting zone, the position of medicaments in each others' shadow can be anticipated, and only one linear positional sensing array can provide multiple medicament resolution.

Resolving medicament dispensing problems:

An Archimedes screw based dispensers offer both speed and good singulation. An Archimedes screw positioned above a stationary trough which allows medicament to fall back over the side of the trough into the medicament supply bin instead of getting jammed provides reliable dispensing. No jam-up prone restrictive channels are used. Pharmacy personnel set-up has been replaced by a machine self learn mode.

Providing error recovery means.

Error recovery is by means of a medicament holding and return system. Immediate counts that, if added to the vial, would cause an over count, are returned to the medicament supply bin. The process is iterated until the correct count can be achieved.

Provision for medicament dispensing and prepackaged medication in one system:

Ample, multi conveyor area is provided for collation of both medicament vials and pre-packed medication.

Modularity provides both medicament and pre-packaged dispensing in one system.

Efficient use of pharmacy floor space and costs:

The volume of medicament supply bins is very efficiently applied resulting in the best use of floor space. Modularization allows system growth to customers requirements and their budgets.

Through simplification, this invention is cost effective to purchase and operate. This makes return of investment a reality.

The greater degree of automation, increased speed, collation and accuracy of dispensing, allows the pharmacists more peace of mind and quality time with their patients. The system cost effectiveness results in a quicker realization of return on investment. By adequately addressing pre-packaged medication, the invention becomes viable as an export product.

BRIEF DESCRIPTION OF THE SEVERAL VIEWS OF THE DRAWINGS

FIG. 2 a. Top view of medicament supply bin.

FIG. 2 b. Cross section view of medicament supply bin.

FIG. 2 c. Isometric view of medicament supply bin with return path.

FIG. 2 d. Medicament slide from medicament supply bin with medicament obscured in shadow of adjacent medicament.

FIG. 2 e. Orthogonal front view of 2d.

FIG. 2 f. Orthogonal front view of 2d.

FIG. 3 a. General view of vial dispenser with label applicator visible below.

FIG. 3 b. Detail view of vial dispenser with vial inverted in arm-gripper.

FIG. 3 c. View of vial dispenser with prong in the receive position.

FIG. 3 d. View of vial dispenser with prong in the label applicator position.

FIG. 4 a. Pre-packed medications storage and transport, general isometric view.

FIG. 4 b. Pre-packed medications storage and transport, side view.

DETAILED DESCRIPTION OF THE INVENTION

Detailed Description

Figure 1:
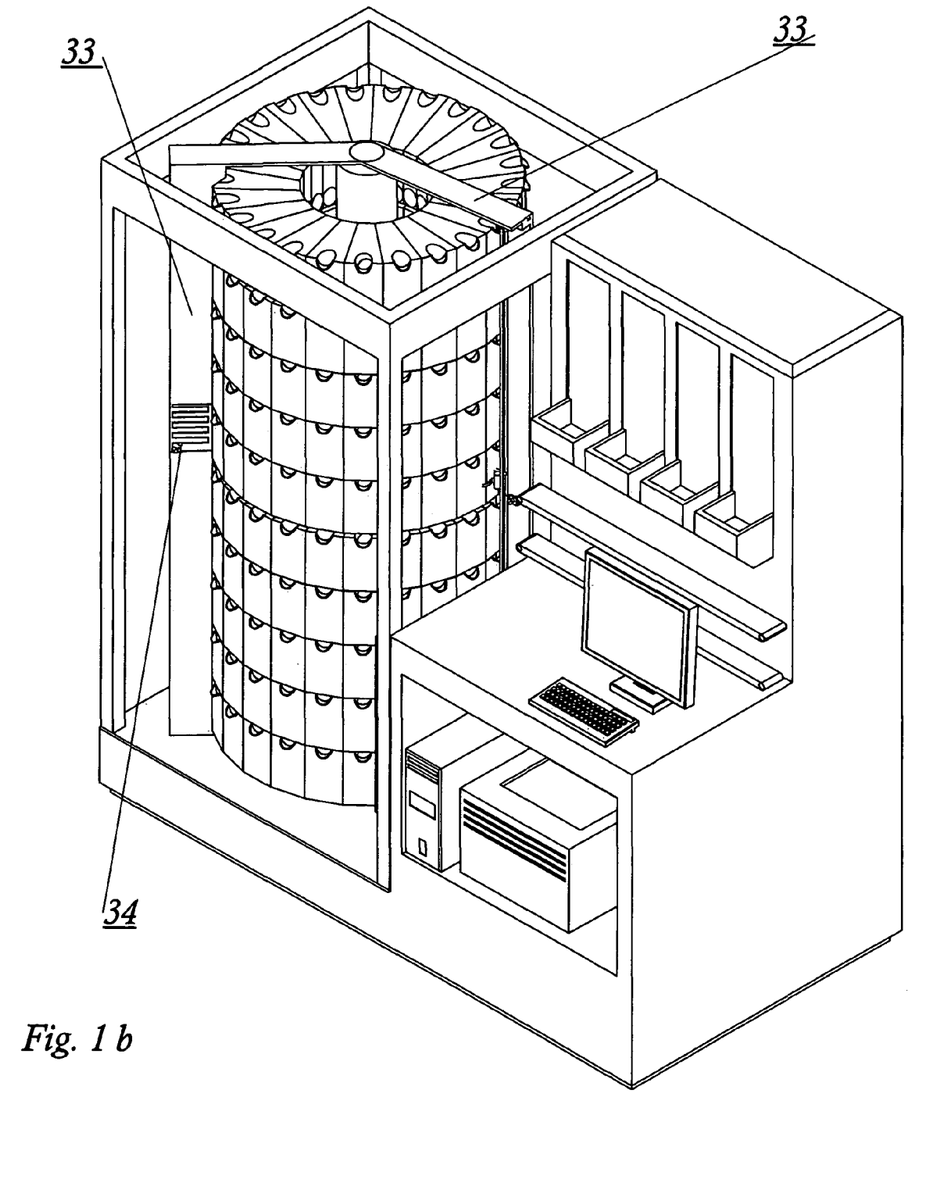
FIG. 1a. General view of Automated dispenser for medicament and pre-packaged medications arranged in rows and columns.
FIG. 1b. General view of Automated dispenser for medicament and pre-packaged medications arranged as a multi-level carousel.
Figure 1A:
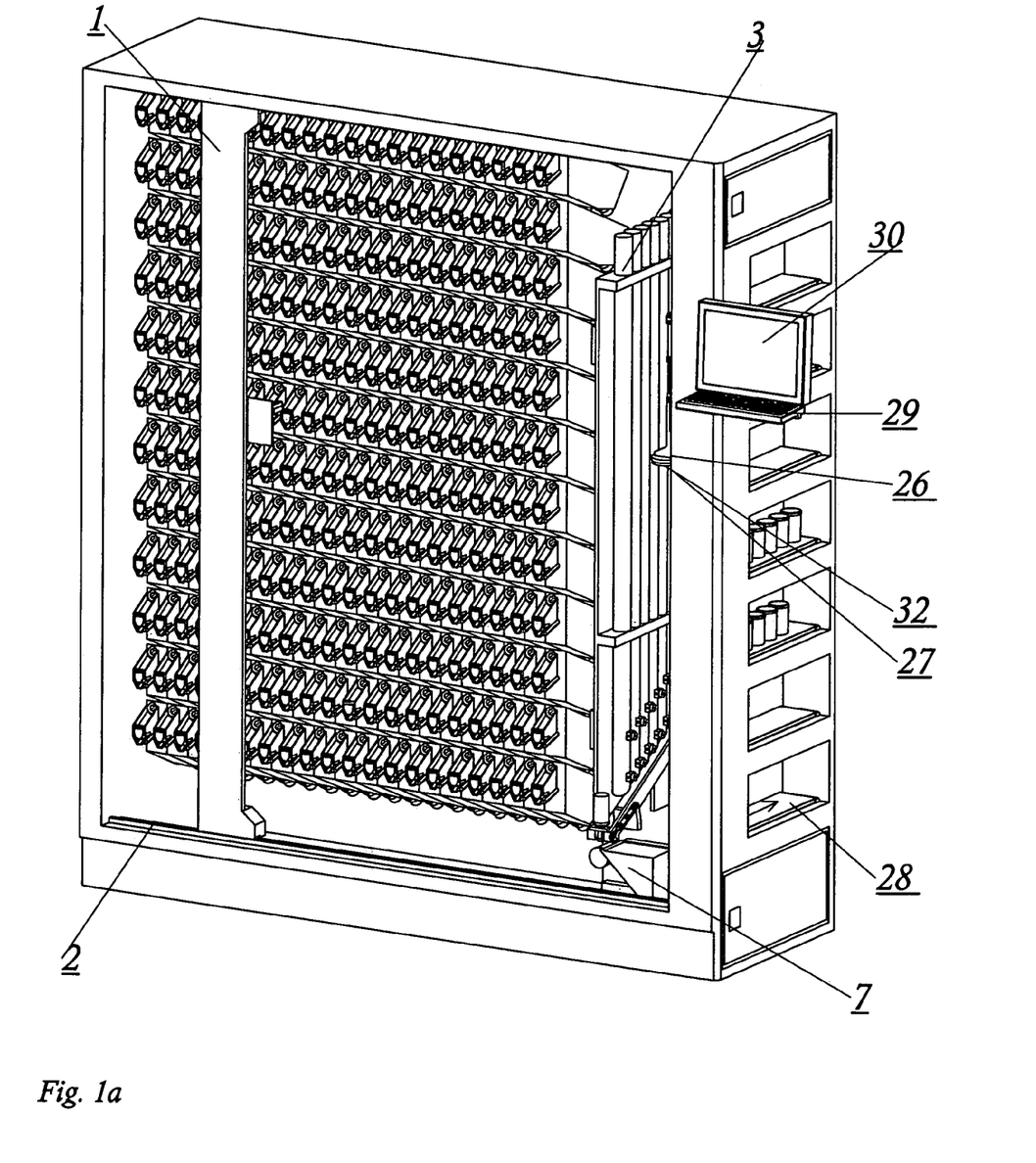

FIG. 1a shows a general view of medicament vials and robotic arms in a column and row configuration. This view shows touch screen computer, 30 and keyboard 29. Each robotic arm is provided with a column vertical elevator moving means 1 and a horizontal moving means 2. The robotic head is pivotal to engage one side for a single sided configuration or both sides, of a paired, dual sided configuration. FIG. 1b indicates a multi-level carousel configuration. The vertical elevator carries the gripper 34, while the rotary movement is provided by arm 33.

Figure 3A:
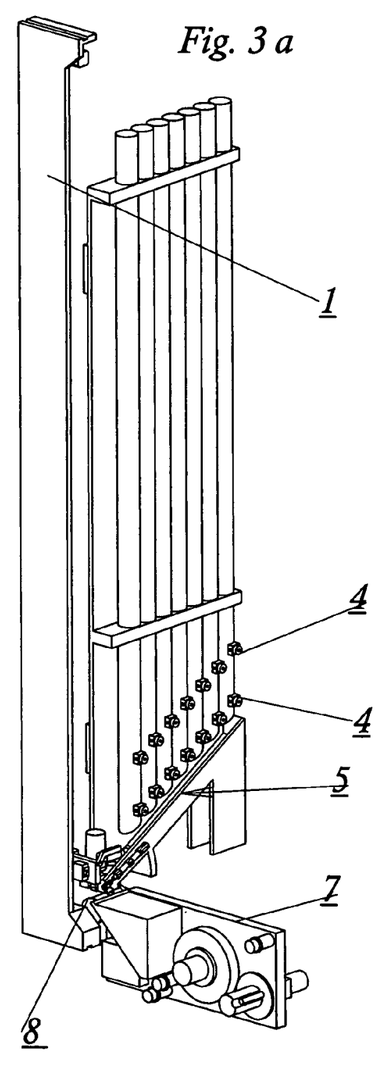
Figure 3B:
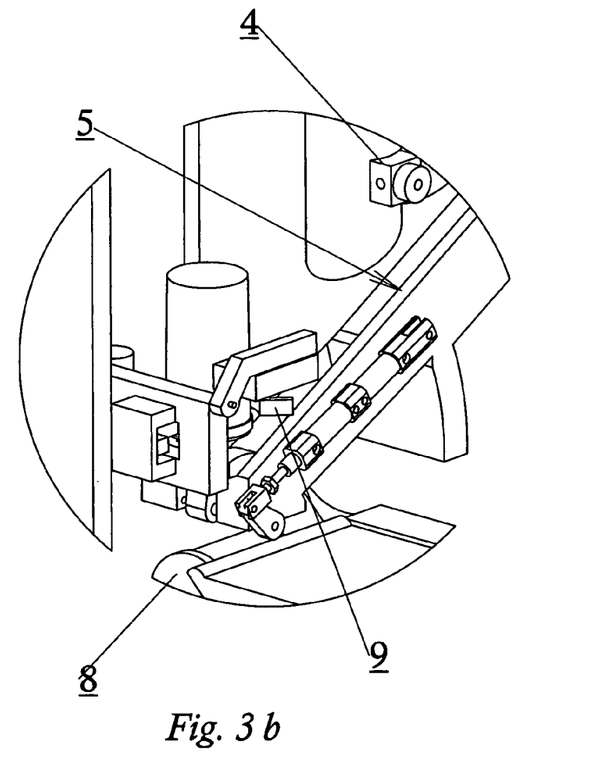
Figure 3C:
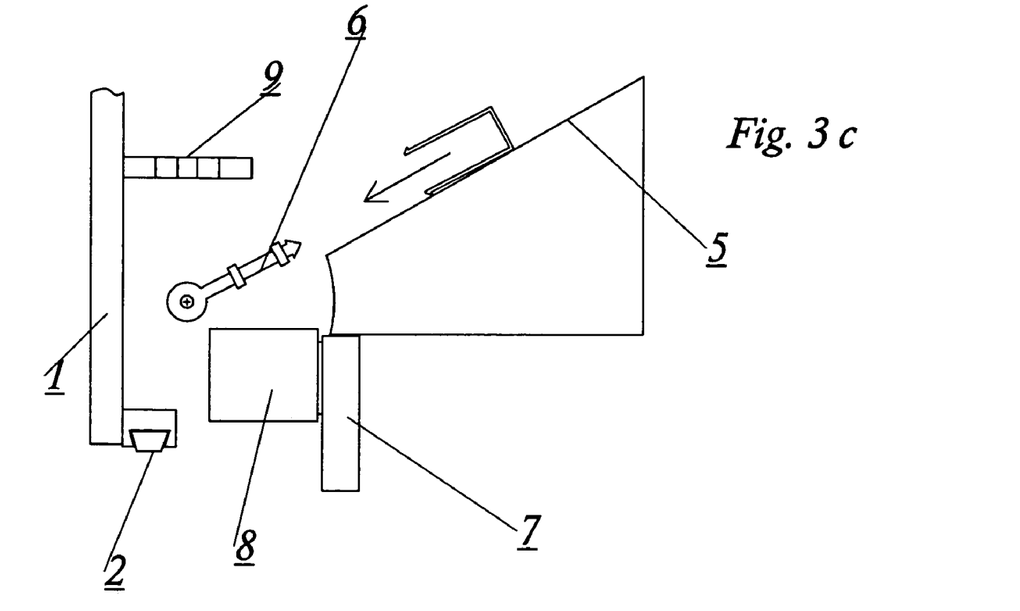
Figure 3D:
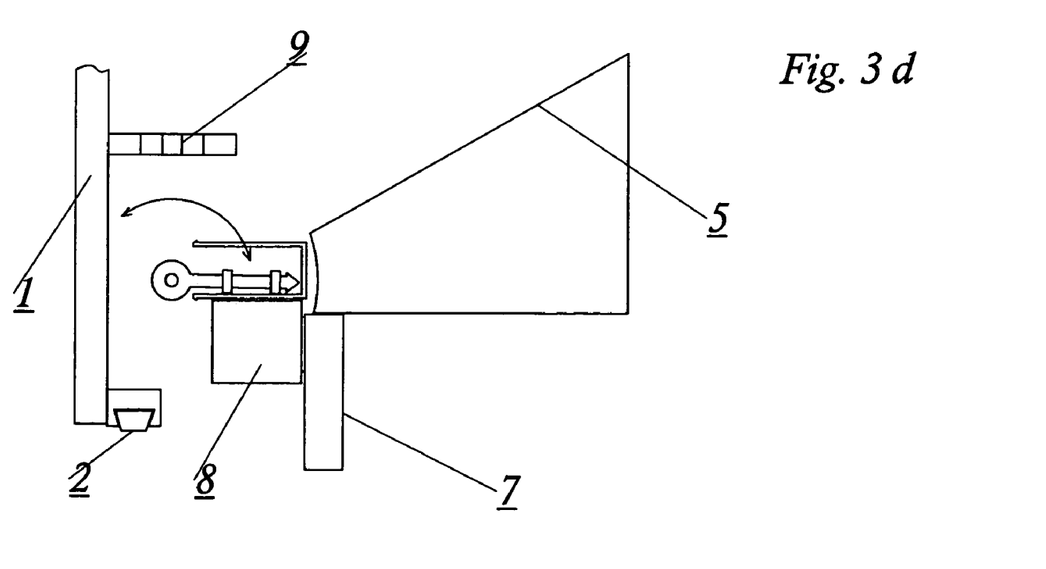

The robotic arm's operational equipment comprises a simple passive, spring loaded claw to grip the vial. Empty vials of various sizes are dispensed from a space saving vertical Cartesian matrix, 3, in FIG. 1 a. A required vial is released by toggling of the support holders 4 in FIG. 3 a. After release the vial slides down the trough, 5, open end first, onto the prong equipped with rollers 6. See printer/labeler, 7. Once a vial is positioned over the prong 6, the prong pivots down to press the vial against the labeler capston 8. The capstan, 8, rolls the vial for label application. After labeling the vial is turned up to a vertical position. The mechanism 9, FIG. 3 b, is the spring loaded claw for holding the vial. The robotic arm lifts and inverts the vial and then moves to the medicament dispensing position.

Figure 2A:
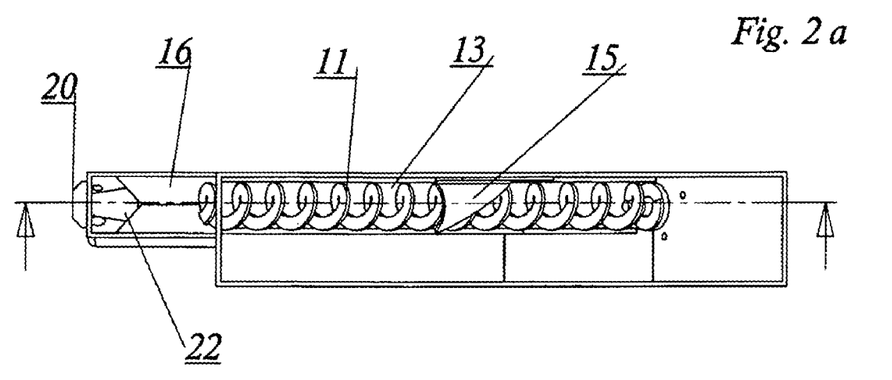
Figure 2B:
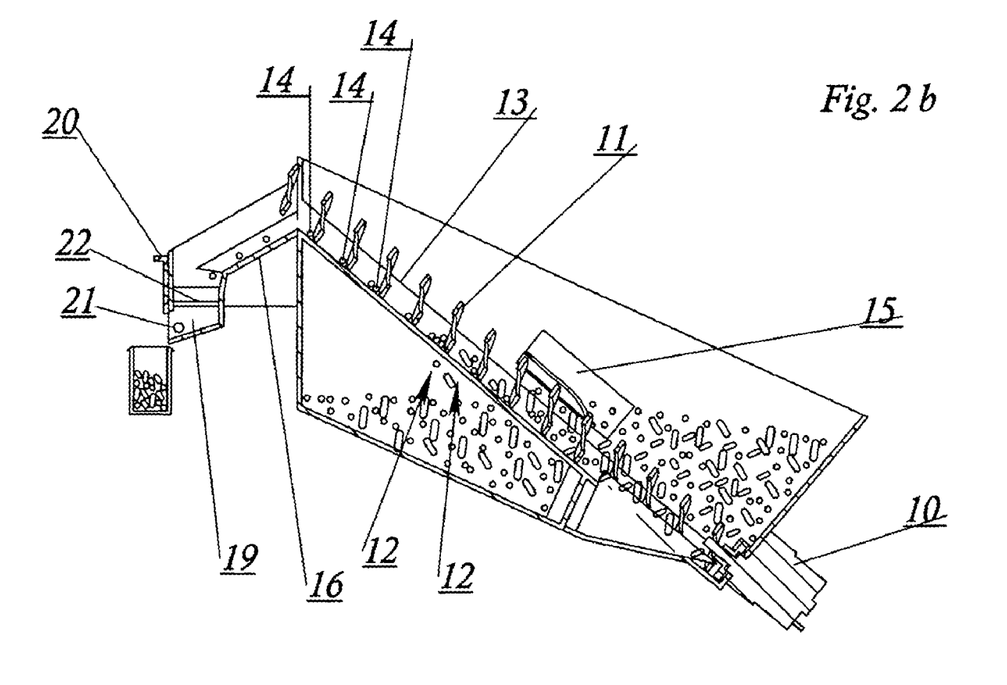
Figure 2C:
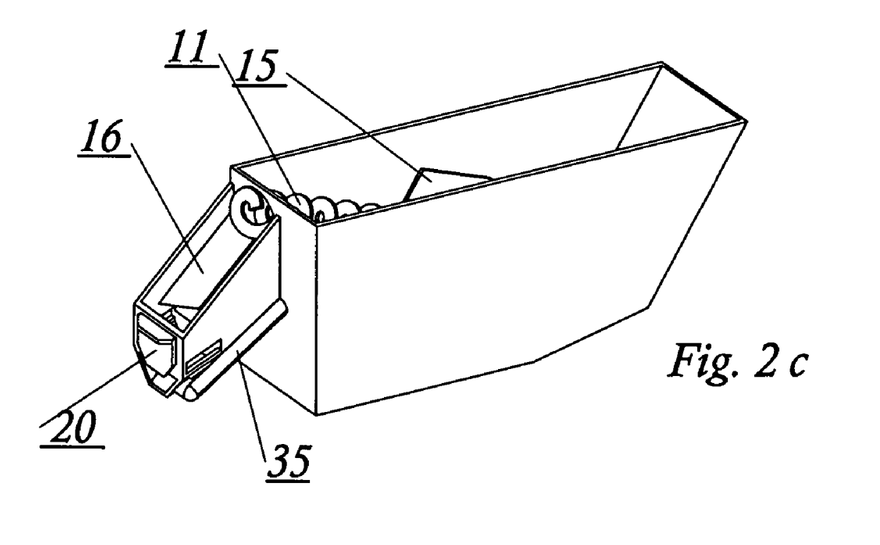
Figure 2D:
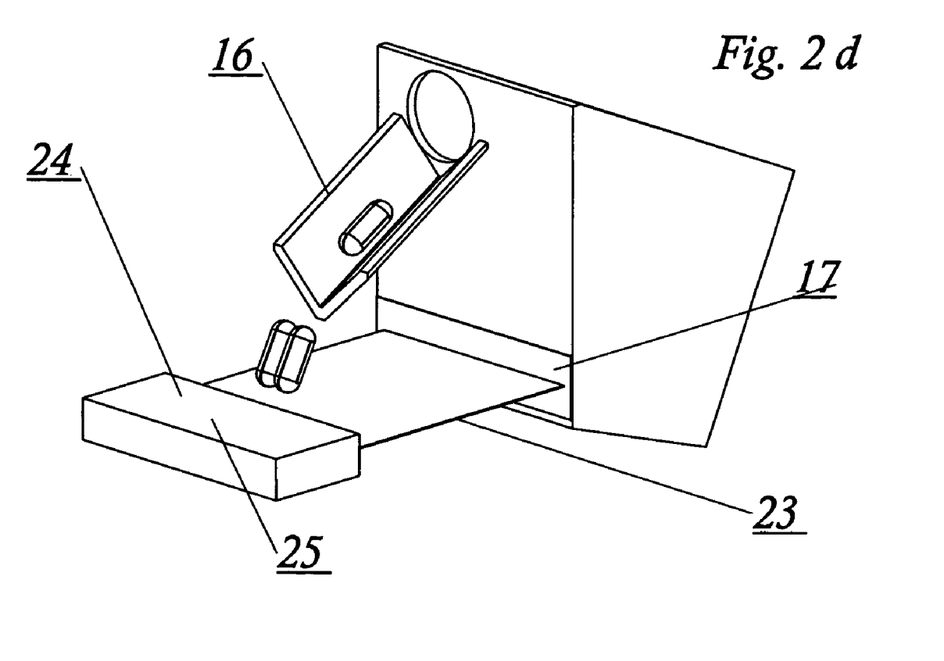
Figure 2E:
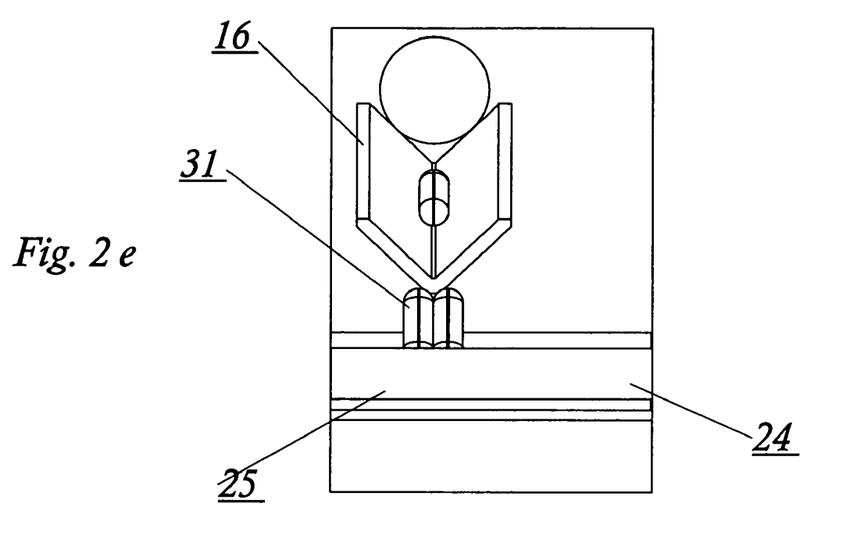
Figure 2F:
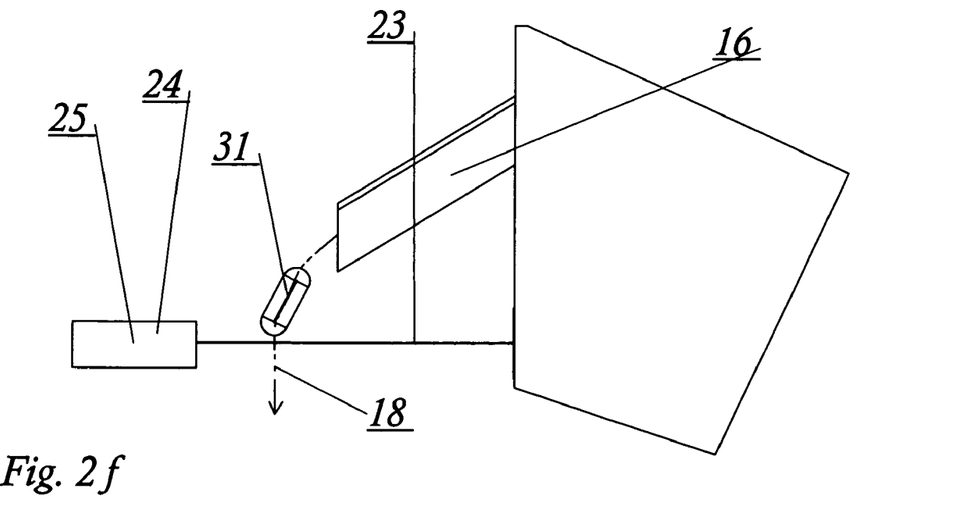

FIG. 2a, 2 b and FIG. 2 c show details of the medicament supply bin with an inclined Archimedes screw with rotate able helix and a fixed open top trough. The helix is driven by direct current motor, 10, to raise medicaments up the trough from the bottom to top of the helix, 11. Once the medicaments on the helix rise above the medicament supply bin medicament level, the inclination of generally 40 degrees causes excess medicaments 12, to tumble back out of the trough, 13, with good singulation on the remaining medicaments, 14 in the trough. The angle (pitch) of the helix and the smoothness of the trough are predetermined to exclude the possibility of friction leading to pinching of the medicaments but to rather singulate them towards the helix top, or fall out of the open top slot of the trough. The stationary open top trough and the rotational helix are self regulating and clearing, making jam-ups virtually impossible. Guide 15, holds the helix down in the trough. Rotational speed of the helix is self learning and manipulated in software for the various medicament sizes. At the top of the helix the medicaments fall onto a slide, 16, to further increase singulation. Those skilled the science will agree that all medicaments move down the slide at very close to the same speed. This implies that, due to the constant of gravity, and almost equal starting velocity, all the medicaments must follow very close to the same trajectories 18. Round medicaments are typically unstable, but by running down the trough are imparted a rotational movement on exiting the dispenser. This rotation gives these medications, anti-tumble stability through gyroscopic action.

The further implication is thus that concurrently falling medicaments are side by side 31 as seen in FIG. 2 d. FIG. 2 e is a view at 90 degrees to the trough showing one medicament being obscured by another. FIG. 2d, using light emitter 24 and light sensor array 25, to monitor detection laminar zone 23, is the basis of using only one charge coupled device (CCD) or CMOS array. From this angle, being orientated, it can be determined if one, two or three medicaments are present to be counted. This process is by a very high speed digital signal processor (DSP). The parameters of each and every medicament supply bin is continuously learned and, together with other medicament supply bin specific parameters, updated to a data base. The reference strip is 17. When commencing vial filling at a new medicament supply bin, the appropriate parameters are retrieved from the data base to precisely control all aspects of the dispensing.

After leaving the laminar detection counting zone, the medicaments pass down to a special holding zone, 19. This holder is equipped with a selectable exit means. Door 20 passes the medicaments to the vial, or a return means to return them to the medicament supply bin. The counting plane is 22. This return means to medicament supply bin could be by air jet, 21. The return channel is 35. During normal initial counting, this selectable means routes the medicaments to the vial with the door, 20, open. As the total count is approached the medicaments' free path to the vial is closed and the medicaments are held back in the holder. At this point the count in the holding area is monitored to ascertain that the total of vial contents plus holding contents does not exceed the total count. Should this be the case the medicaments in the holding section are returned to the medicament supply bin and the system continues iteration until the right count is achieved. In one embodiment the return means of the medicament holding system could be an air jet and in another the means could be an electric solenoid. A concurrent multitasking embodiment is envisaged where the final count can held in the output chute until it can be serviced by the robot arm. Vial drop off position is 27 (only one shown), with release mechanism 26 (only one shown). Medication collation is on multiple rows, 28. FIG. 1 a shows an arrow on medication collation conveyor 28 to show direction of travel after vial has been dropped of on conveyor by vial gripper-arm. At 32, an electronic ID device is attached for locating the different items of a specific patient's prescription.

A fiber optic linking system, not shown in the drawings, is arranged with interfacing connectors between the frame and medicament supply bins so that a signal being carried by the link would be interrupted if a medicament supply bin was removed. This interruption would indicate a medicament supply bin was moved and would initiate a system scan, using the robotic arm equipped with a scanner and indicia on each medicament supply bin, to ascertain and log the position of all medicament supply bins to a data base.

Figure 4A:
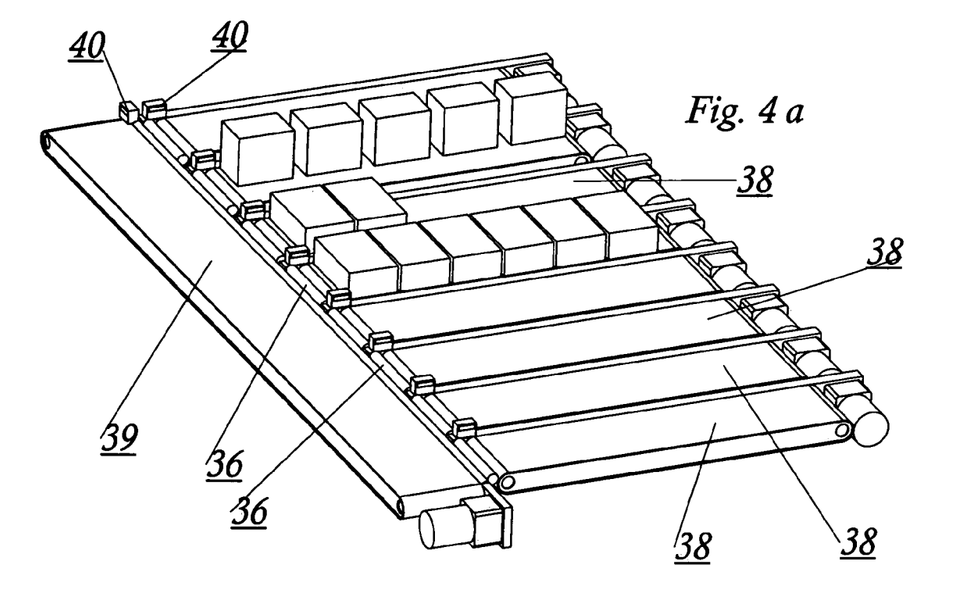
Figure 4B:
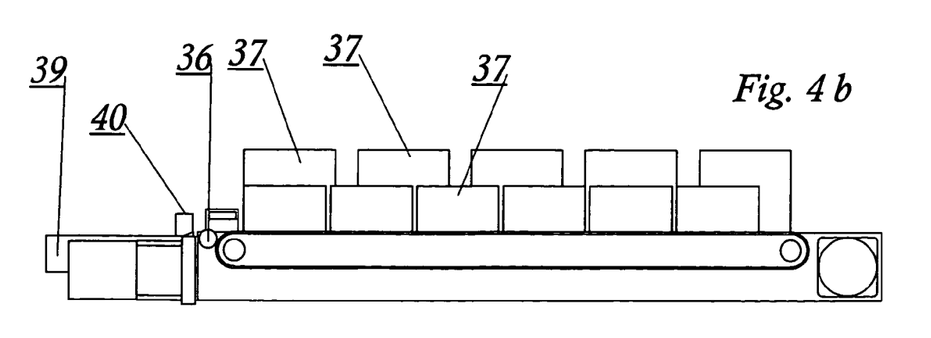

In FIGS. 4 a and 4b, pre-packed medication, 37, is housed on pre-packed bulk supply conveyors, 38, which may, depending on size of medication, be in stacked or linear form. If in stacked form, a minimal restraint arm would allow the top remaining quantity to be stacked one position down when the conveyor, with greater friction, withdraws the bottom pre-pack from the stack one by one. If stacking is due to shape or dimensions not possible, the larger pre-packed medications lie flat on the pre-packed bulk supply conveyor. At the end of each pre-packed bulk supply conveyor is an independently driven roller, 36, with higher frictional coating than the conveyors. Light sensor 40 initiates the transfer to the roller 36 to the transfer conveyor 39. As the medication traverses this roller, its weight on the roller, which is very slightly higher than either the conveyors, causes increased force and thus friction on the roller to move the medication over to the next conveyor.

Holding conveyors can be coupled together to form larger compartments.

Additional Applications

The medicament counting accuracy of the dispensing means, as detailed above, lends itself to an embodiment of a general purpose, desk top medicament counter. Yet another embodiment is, in stead of dispensing to vials, to dispense to a central chute system for take off to a pouch or bagging system.

CONCLUSION

The improvements under the present invention provide new wide ranging performance improvements beyond the expectancy of the changes. The greater degree of automation, increased speed, collation and accuracy of dispensing, allows pharmacists more peace of mind and quality time with patients. The system cost effectiveness results in a sound business model with quick realization of investment. By adequately addressing pre-packaged medication, the invention becomes viable as an export product.

What is claimed and desired to be secured by Letters Patent is as follows:

1. An automated medicament dispensing machine for dispensing and counting individual medicaments, comprising:
   a programmable dispensing control system programmed to control said automated medicament dispensing machine,
   at least one vial bulk supply bin for storing and dispensing vials;
   a plurality of medicament supply bins, wherein each medicament supply bin comprises:
      a dispenser for dispensing medicaments into said vials, and
      a slide for:
         imparting rotational spin to round medicaments, and
         orientating concurrently dropped medicaments side-by-side,
   a robotic arm,
   a vial gripper attached to said robotic arm, said vial gripper comprising:
      a sensor system carried on said vial gripper, said sensor system defining a laminar counting plane through which medicaments fall, said sensor system comprising:
         an optical emitter for illuminating said laminar counting plane,
         an optical receiving array with individually monitored pixels, adopted to monitor optical signals generated by said optical emitter that have been reflected off said individual medicaments as they pass through said laminar counting plane, and
         a digital signal processor positional computing means for analyzing pixel patterns produced by said optical receiving array and for informing said dispensing control system of the correct number of medicaments simultaneously passing through said laminar counting plane
   wherein said optical emitter and optical receiving array are positioned so that medicaments that fall together are positioned side-by-side with respect to the optical emitter and receiving array and not one in front of the other so as to obscure one of the medicaments.

2. The automated medicament dispensing machine as in claim 1, further comprising a data base linked to each of said plurality of medicament supply bins, wherein said digital signal processor positional computing means continually learns and updates parameters to said database for retrieval on new dispensing sessions.

3. The automated medicament dispensing machine as in claim 1, wherein said plurality of medicament supply bins is an array of medicament supply bins and wherein said illumination means and said optical receiving array are controlled via said programmable dispensing control system to count individual medicaments from said array of medicament supply bins.

4. The automated medicament dispensing machine as in claim 1, comprising:
   a medicament supply bin for storing a plurality of medicaments, and
   a "C" shaped open trough Archimedes screw comprising:
      a lower end, wherein said lower end is inserted into said medicament supply bin, and
   wherein medicaments are removed from said medicament supply bin for dispensing by operation of said "C" shaped open trough Archimedes screw.

5. The automated pharmaceutical medicament dispenser as in claim 4, wherein said "C" shaped open top section trough may be adjustably positioned to facilitate medicament dispensing.

6. The automated pharmaceutical medicament dispenser as in claim 1, wherein said slide comprises a "V" shaped trough.

7. The automated pharmaceutical medicament dispenser as in claim 1, wherein said optical emitter and said optical receiving array are located on the same side of said medicament detection counting plane.

8. An automated pharmaceutical medicament dispenser for automatically dispensing medicaments into at least one vial, comprising:
   a plurality of medicament supply bins each for holding a plurality of medicaments,
   a medicament dispenser comprising an open trough Archimedes screw inserted into said plurality of medicaments for retrieving medicaments for dispensing,
   an electronic optical sensor counter for counting said medicaments as said medicaments leave said medicament dispenser,
   a medicament holding and return device for holding said counted medicaments prior to being dispensed into said at least one vial, wherein said medicament holding and return device comprises a means for returning excess medicaments to said medicament supply bin when said counter detects an excess of said medicaments at said medicament holding and return device, wherein said medicament dispenser repeats dispensing to said medicament holding and return device until said counter verifies the right count has been achieved at said medicament holding and return device,
   a robotic arm for placing said at least one vial adjacent to said medicament holding and return device so that said counted medicaments can be dispensed into said at least one vial, and said robotic arm for transferring said at least one vial to a user accessible area for user retrieval of said at least one vial, and
   a programmable control system for controlling the operation of said medicament dispenser, said counter, said medicament holding and return device, and said robotic arm.

9. The automated pharmaceutical medicament dispenser as in claim 8, wherein said means for returning excess medicaments to said medicament supply bin comprises a device for blowing compressed air to blow said excess medicaments back to said supply bin.

10. The automated pharmaceutical medicament dispenser as in claim 8, wherein said means for returning excess medicaments to said medicament supply bin is an electric solenoid.

11. The automated pharmaceutical medicament dispenser as in claim 8, wherein medicaments are counted by said electronic optical sensor counter and held by said medicament holding and return device while said robotic arm is simultaneously in motion to maximize dispensing efficiency.

12. The automated pharmaceutical medicament dispenser as in claim 8, further comprising a security device for monitoring the removal of said a plurality of medicament supply bins, said security device is a fiber optic linked system in electrical communication with said programmable control system, wherein said programmable control system is programmed to initiate a search and update of the positional database of said plurality of said medicament supply bins upon the removal of any of said plurality of said medicament supply bins.

13. An automated pharmaceutical medicament dispenser for automatically dispensing medicaments into a channel for bagging, comprising:
- a plurality of medicament supply bins each for holding a plurality of medicaments,
- a medicament dispenser inserted into said plurality of medicament supply bins,
- a sensor system defining a laminar counting plane through which medicaments fall, said sensor system comprising:
  - an optical emitter for illuminating said laminar counting plane,
  - an optical receiving array with individually monitored pixels, adopted to monitor optical signals generated by said optical emitter that have been reflected off said individual medicaments as they pass through said laminar counting plane, and
  - a digital signal processor positional computing means for analyzing pixel patterns produced by said optical receiving array and for informing said dispensing control system of the correct number of medicaments simultaneously passing through said medicament detection counting plane
- a medicament holding and return device for holding said counted medicaments prior to being dispensed into said at least one vial, wherein said medicament holding and return device comprises a means for returning excess medicaments to said medicament supply bin,
- a robotic arm for placing said at least one vial adjacent to said medicament holding and return device so that said counted medicaments can be dispensed into said at least one vial, and said robotic arm for transferring said at least one vial to a user accessible area for user retrieval of said at least one vial, and
- a programmable control system for controlling the operation of said medicament dispenser, said electronic optical counter, and said medicament holding and return device.

14. The automated pharmaceutical medicament dispenser as in claim 13, wherein said optical emitter and optical receiving array are positioned so that medicaments that fall together are positioned side-by-side with respect to the optical emitter and receiving array and not one in front of the other so as to obscure one of the medicaments.

* * * * *